United States Patent
Ye et al.

(10) Patent No.: US 9,795,021 B2
(45) Date of Patent: Oct. 17, 2017

(54) X-RAY EQUIPMENT AND ALIGNMENT METHOD OF X-RAY EQUIPMENT

(71) Applicant: GE MEDICAL SYSTEMS GLOBAL TECHNOLOGY CO. LLC, Waukesha, WI (US)

(72) Inventors: Bin Ye, Beijing (CN); Yannan Huang, Beijing (CN); Li Tao, Beijing (CN)

(73) Assignee: GENERAL ELECTRIC COMPANY, Schenectady, NY (US)

(*) Notice: Subject to any disclaimer, the term of this patent is extended or adjusted under 35 U.S.C. 154(b) by 288 days.

(21) Appl. No.: 14/580,659

(22) Filed: Dec. 23, 2014

(65) Prior Publication Data

US 2015/0185340 A1 Jul. 2, 2015

(30) Foreign Application Priority Data

Dec. 31, 2013 (CN) .......................... 2013 1 0751756

(51) Int. Cl.
*A61B 6/08* (2006.01)
*H05G 1/02* (2006.01)
*A61B 6/04* (2006.01)

(52) U.S. Cl.
CPC ............. *H05G 1/02* (2013.01); *A61B 6/0492* (2013.01)

(58) Field of Classification Search
CPC ......... A61B 6/0492; A61B 6/587; A61B 6/14; A61B 6/4283; A61B 6/547; A61B 6/4405; A61B 6/4291; A61B 6/548; A61B 6/583; A61B 6/032; A61B 6/4452; A61B 2090/363; A61B 6/06; A61B 6/145; A61B 6/4021; A61B 6/487; A61B 6/502; A61B 6/505; A61B 6/00; H05G 1/02; G03F 7/031; G03F 7/0007; G03F 7/0045; G03F 7/027; G03F 7/2002; G03F 7/2037; G03F 7/30; G03F 7/029; G03F 7/105; G03F 7/20; G03F 7/2039; G03F 7/001; G03F 7/0037; G03F 7/32
USPC ...... 378/197, 193, 198, 205, 206; 250/522.1
See application file for complete search history.

(56) References Cited

U.S. PATENT DOCUMENTS

| | | | |
|---|---|---|---|
| 6,435,716 B1 * | 8/2002 | Polkus ................. | A61B 6/4233 378/197 |
| 6,702,459 B2 * | 3/2004 | Barnes ................. | A61B 6/4405 250/522.1 |
| 6,821,017 B1 * | 11/2004 | Tankersley ........... | A61B 6/4429 378/205 |
| 7,581,884 B1 * | 9/2009 | Barnes ..................... | A61B 6/06 378/164 |
| 8,867,705 B2 * | 10/2014 | Lalena ..................... | A61B 6/08 378/166 |

* cited by examiner

*Primary Examiner* — Irakli Kiknadze
(74) *Attorney, Agent, or Firm* — GE Global Patent Operations; Mark A. Vivenzio

(57) ABSTRACT

The present invention provides an X-ray equipment and an alignment method thereof. The X-ray equipment comprises a tube, a detector, an LED array, a camera and a display. The LED array is fixed relative to a detection center of the detector, and has a predefined geometric center; the camera is fixed relative to a center of the tube, for photographing the LED array; the display is connected to the camera, for displaying images photographed by the camera, wherein when the center of the tube is aligned with the detection center of the detector, the geometric center of the LED array is located on a specific pixel unit on the display.

18 Claims, 6 Drawing Sheets

X-RAY EQUIPMENT AND ALIGNMENT METHOD OF X-RAY EQUIPMENT

TECHNICAL FIELD

The present invention relates to an X-ray equipment and an alignment method thereof, in particular, relates to an X-ray equipment and an alignment method thereof for use in medical treatment.

BACKGROUND OF THE INVENTION

In the existing X-ray medical detecting devices, in order to align the center of a tube with the center of a detector before exposure, and to obtain a better Source Image Distance (SID), a radiographer needs to manually adjust the position of detector housing or tube.

Obviously, manual adjustment cannot achieve the effect of precise alignment, thereby affecting imaging quality. In the prior art, a position encoder can also be integrated in the equipment to precisely control the position of the tube and detector, so as to obtain a better alignment effect, but this manner requires a great number of position encoders, thereby leading to a higher cost. Meanwhile, due to impacts of mounting positions, in many occasions, position encoders require mounting of gears and toothed belts, with positioning precision subjected to transmission of mechanical devices and failures occurring easily.

Hence, a novel X-ray equipment and an alignment method thereof need to be provided, so as to obtain a better alignment effect.

BRIEF SUMMARY OF THE INVENTION

One illustrative example of the present invention provides an X-ray equipment, comprising a tube, a detector, an LED array, a camera and a display. The LED array is fixed relative to a detection center of the detector, and has a predefined geometric center. The camera is fixed relative to a center of the tube, for photographing the LED array. The display is connected to the camera, for displaying images photographed by the camera; when the center of the tube is aligned with the detection center of the detector, the geometric center of the LED array is located on a specific pixel unit on the display.

Another illustrative example of the present invention further provides an alignment method of X-ray equipment, comprising photographing step and displaying step. The photographing step photographs an LED array via a camera, wherein, the camera is fixed relative to a center of a tube of an X-ray equipment; the LED array is fixed relative to a detection center of a detector of the X-ray equipment, and has a predefined geometric center. The displaying step displays via a display images photographed by the camera; when the center of the tube is aligned with the detection center of the detector, the geometric center of the LED array is located on a specific pixel unit on the display.

Other features and aspects will become much clearer through the following detailed depictions, drawings and claims.

BRIEF DESCRIPTION OF THE DRAWINGS

The present invention can be better understood by depicting the illustrative examples of the present invention in combination with the following drawings, wherein.

DETAILED DESCRIPTION OF THE INVENTION

The specific embodiments of the present invention will be depicted below; it should be indicated that, during the process of specifically depicting these embodiments, in order to make a concise depiction, it is impossible for the present description to make detailed depiction to all features of the actual embodiments. It should be understood that, during the actual implementing process of any one embodiment, e.g., during the process of any one engineering project or designing project, in order to realize specific objectives of developers, and to meet system related or commerce related limits, usually various specific decisions will be made, such that a transition from one embodiment to another embodiment will also occur. In addition, it should also be understood that, although efforts as made during the developing process may be complicated and lengthy, for ordinary persons skilled in the art who are related with the contents disclosed by the present invention, some changes in design, manufacture or production on the basis of the technical contents disclosed by the present invention are only customary technical means, and should not be construed as the contents of the present invention being insufficiently disclosed.

Unless defined otherwise, the technical terms or scientific terms that are used in the claims and the description should have general meanings as understood by persons with ordinary skills in the technical field to which the present invention belongs. Such words as "first", "second" used in the description and claims of the present invention patent application do not denote any sequence, quantity or significance, and are only used to distinguish different constituting parts. Such words as "one", "a" or "an" only represent that at least one exists, without denoting quantity limitation. Such words as "including" or "comprising" mean that the elements or objects appearing before the words "including" or "comprising" cover the elements or objects and equivalent elements listed after the words "including" or "comprising", not excluding other elements or objects. Such words as "connection" or "link" are not limited to physical or mechanical connection, and are not limited to direct or indirect connections, neither.

Figure 1:
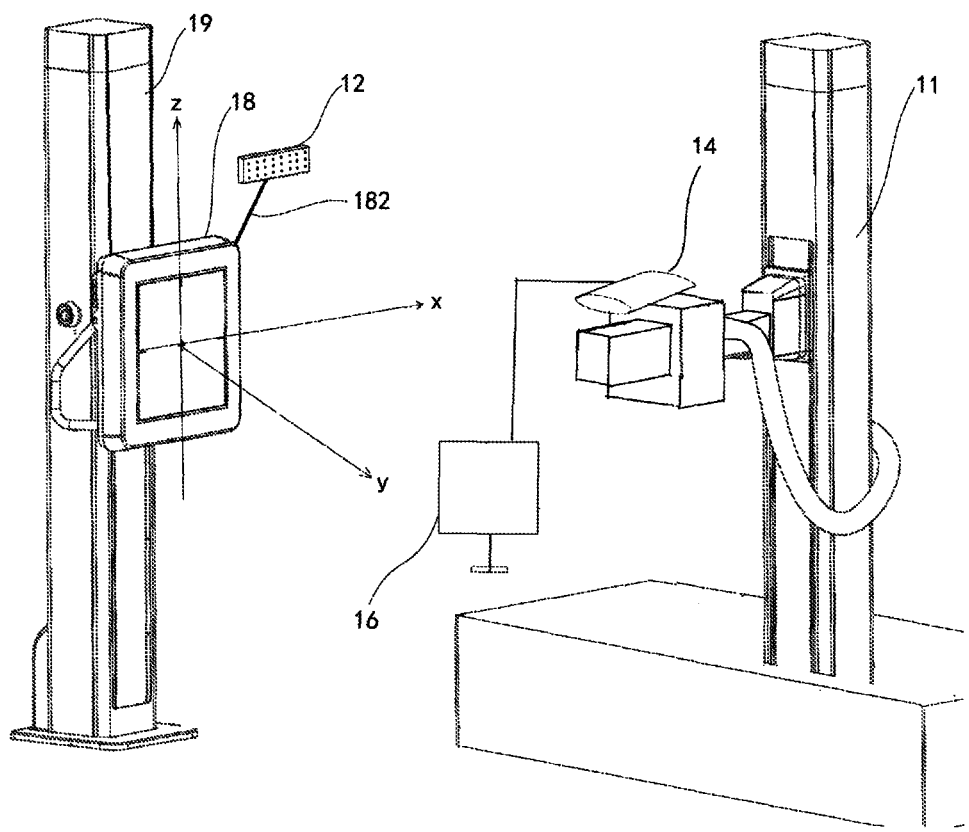
FIG. 1 is a structural diagram of the X-ray equipment provided by one illustrative example of the present invention.
Figure 2:
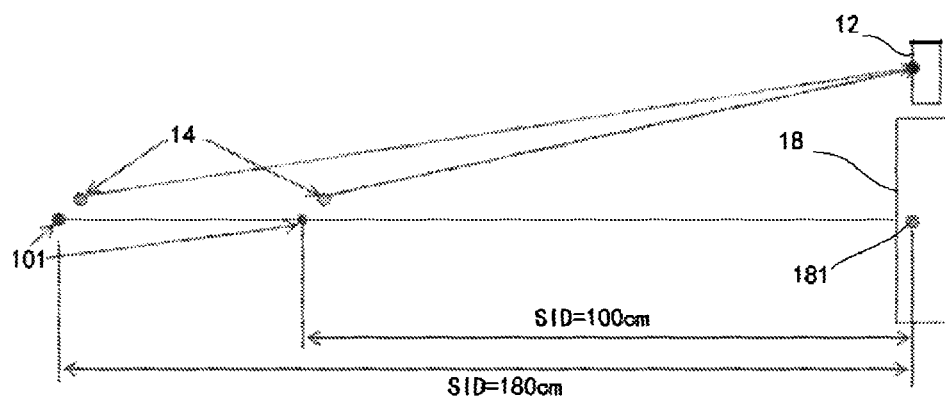
FIG. 2 is an illustrative schematic diagram of the position relation among the camera, the tube, the LED array and the detector in FIG. 1, in the case of different source image distances.
Figure 3:
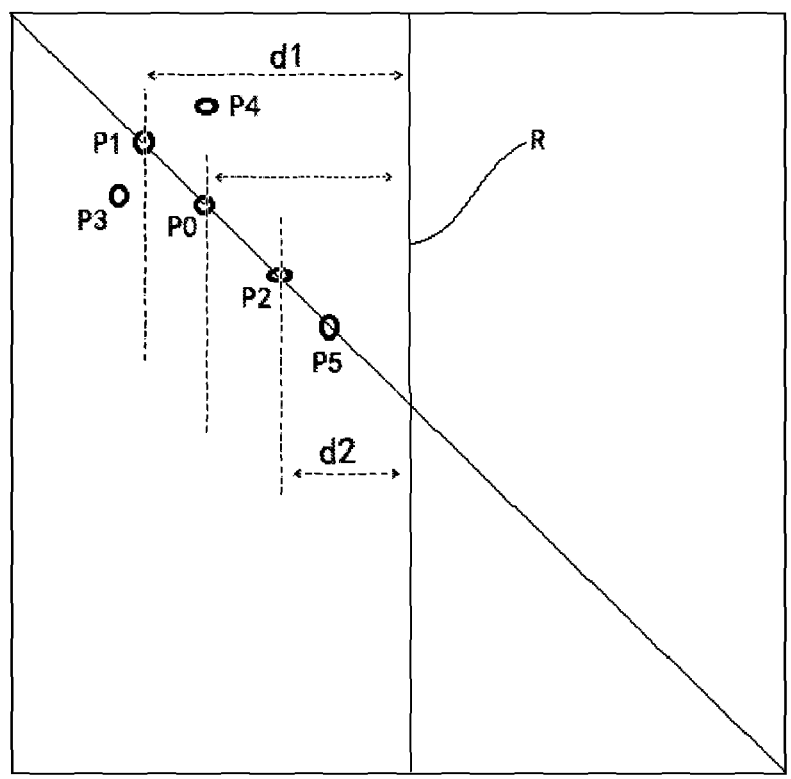
FIG. 3 is an illustrative schematic diagram of relative changes in the position of the geometric center of the LED array on the display, when the relative positions of the center of the tube and the detection center of the detector in FIG. 1 vary.

FIG. 1 is a structural diagram of the X-ray equipment provided by one illustrative example of the present invention; FIG. 2 is an illustrative schematic diagram of the position relation among the camera, the tube, the LED array and the detector in FIG. 1, in the case of different source image distances; FIG. 3 is an illustrative schematic diagram of relative changes in the position of the geometric center of the LED array on the display, when the relative positions of the center of the tube and the detection center of the detector in FIG. 1 vary. As shown in FIGS. 1 to 3, the X-ray equipment in the present example is a vertical X-ray equipment comprising a tube (not shown) and a detector 18; the tube is mounted on a tube column 11; the detector 18 is mounted on a sternum stand 19; the tube has a center 101, and the detector 18 has a detection center 181, which specifically can be a center of the detection plane of the detector 18. During detection, the center 101 of the tube is aligned with the detection center 181 of the detector 18; after penetrating a patient subject, the X-rays that are emitted by the tube in the horizontal direction (the y-axis direction in FIG. 1) are detected by the detector 18; image information of a detected site can be formed by treating the detected signals.

The X-ray equipment further comprises a Light Emitting Diode (LED) array 12, a camera 14 and a display 16. The LED array 12 is fixed relative to the detection center 181 of the detector 18. The camera 14 is fixed relative to the center 101 of the tube, for photographing the LED array 12. The display 16 is connected to the camera 14, for displaying images photographed by the camera 14. Specifically, the display 16 can be connected to the camera 14 via a signal transmission module, and receive images photographed by the camera 14.

Since the camera 14 is fixed relative to the center 101 of the tube, and the LED array 12 is fixed relative to the detection center 181 of the detector 18, via a coordinate conversion, the position relation of the geometric center of the LED array 12 in the image photographed by the camera 14, can be converted to the position relation of the center 101 of the tube relative to the detection center 181 of the detector 18; conversely, the position relation when the center 101 of the tube is aligned relative to the detection center 181 of the detector 18, can also be represented by the position of the geometric center of the LED array 12 in the display 16, for convenient depiction, the pixel unit of which position referring to a "specific pixel unit".

In other words, when the center 101 of the tube is aligned relative to the detection center 181 of the detector 18, after the display 16 displays the image photographed by the camera 14, the geometric center of the LED array 12 is located on the specific pixel unit on the display 16. Through this manner, only by observing the position of the geometric center of the LED array 12 on the display 16, with manual or automatic operation, the radiographer can realize the alignment of the center of the tube with the center of the detector; alignment precision is high, and operation is intuitive and convenient, so a better alignment effect is obtained.

As shown in FIG. 3, the position of the specific pixel unit on the display is specifically as follows: located between pixel units P1 and P2 on a line connecting the pixel units P1 and P2. The pixel unit P1 is: the position of the geometric center of the LED array 12 on the display 16, when the center 101 of the tube is aligned with the detection center 181 of the detector 18, and the source image distance is a lower critical value (e.g., 100 cm); the pixel unit P2 is: the position of the geometric center of the LED array 12 on the display 16, when the center 101 of the tube and the detection center 181 of the detector 18 are in a state of alignment, and the source image distance is a larger critical value (e.g., 180 cm).

Since the centers of the tube and detector of the vertical X-ray equipment are generally in a fixed alignment state in the x-axis direction as shown by FIG. 1, the present example only involves alignment operations in the y-axis and z-axis directions; if the geometric center of the LED array 12 is on the line connecting the pixel units P1 and P2, it means that the center 101 of the tube has been aligned with the detection center 181 of the detector 18 in the z-axis direction; if the geometric center of the LED array 12 is further located between the pixel units P1 and P2, it means the source image distance of the vertical X-ray equipment falls within the stipulated range.

On the contrary, as shown in FIG. 3, when the tube is moved upwards along the z-axis direction, the geometric center of the LED array 12 will move to the position as shown by P3 in FIG. 3; when the tube is moved downwards along the z-axis direction, the geometric center of the LED array 12 will move to the position as shown by P4 in FIG. 3; when the tube is moved along the y-axis direction such that the source image distance goes beyond the range which is defined by the above lower critical value and larger critical value, the geometric center of the LED array 12 may move to the position as shown by P5 in FIG. 3.

In the present example, in order to make the relative position relation among the LED array 12, the camera 14, the tube and the detector 18 more simple, so as to simplify the complexity of coordinate conversion, the photographing direction of the camera 14 is set to be identical to the irradiating direction of the tube (e.g., the center line of the light beam emitted by the camera 14 and the center line of the ray beam emitted by the tube are both parallel to the x-axis direction), the geometric center of the LED array 12 is defined on the light emitting area thereof, and further, the light emitting area of the LED array 12 is located in the same plane with the detection area of the detector 18.

In addition, in order to avoid the body of the detected subject from obstructing the LED array 12, and to ensure the camera to photograph the geometric center of the LED array during detection, the geometric center of the LED array 12 in the present example is set in a manner such that the line connecting it with the detection center 181 of the detector 18 is disposed at a specific angle relative to the longitudinal line (i.e., the line on the detector 18 parallel to the z-axis direction in FIG. 1 and the reference line R in FIG. 3) on the detector 18, i.e., when the center 101 of the tube is aligned with the detection center 181 of the detector 18, viewed from the photographing direction of the camera 14, the line connecting the geometric center of the LED array 12 and the detection center 181 of the detector is disposed at a specific angle relative to the longitudinal line on the detector.

The above LED array 12 specifically can be fixed on the detector 18 through a fixed arm extending from the detector 18; as shown in FIG. 1, a fixed arm 182 extends obliquely and upwards from the detector 18, the LED array 12 is mounted on the fixed arm 182, in a manner such that the geometric center of the LED array 12 is kept unchanged relative to the detection center 181 of the detector 18, and their connecting line is disposed at a specific angle relative to the longitudinal line on the detector 18.

The camera 14 specifically can be mounted on a beam limiter (not marked) fixedly arranged relative to the tube, so as to realize being unchanged relative to the center of the tube.

Alternatively, the X-ray equipment in the present example, further comprises a SID calculation module (not shown) connected to the display 16, for calculating a current source image distance SIDX, based on horizontal pixel offset (dX as shown in FIG. 3) of the pixel unit (P0 as shown in FIG. 3) on which the geometric center of the LED array 12 is located relative to a reference pixel unit (e.g., a pixel unit located on the reference line R as shown in FIG. 3) preset on the display, horizontal pixel offset (d1 as shown in FIG. 3) of the pixel unit P1 relative to the reference pixel unit, and relation between the lower critical value of the source image distance and the larger critical value of the source image distance, under the specific angle.

For example, in the present example, the line connecting the geometric center of the LED array 12 and the detection center 181 of the detector 18 is at an angle of 45 degrees relative to the longitudinal line on the detector 18, so after the center 101 of the tube is aligned with the detection center 181 of the detector 18 in the z-axis direction, in the image displayed by the display 16, the geometric center of the LED array 12 is always located on the line disposed at the angle of 45 degrees relative to the longitudinal line (the reference line R as shown in FIG. 3) in the image. Hence, the SID calculation module specifically can calculate the current source image distance SIDX according to the following formula (1):

$$SIDX = SID1 + (SID2 - SID1)/(dX - d1) \qquad (1).$$

In the above formula, SID X is the current source image distance, SID1 is the lower critical value of the source image distance, SID2 is the larger critical value of the source image distance, dX is the horizontal pixel offset of the pixel unit P0 on which the geometric center of the LED array 12 is currently located relative to the reference pixel unit, and d1 is the horizontal pixel offset of the pixel unit P1 relative to the reference pixel unit.

The setting of the line connecting the geometric center of the LED array 12 and the detection center 181 of the detector 18 to be at an angle of 45 degrees relative to the longitudinal line on the detector 18, not only can avoid the LED array 12 from being obstructed by the detected subject to the maximum extent, and ensure the camera 14 to photograph it, but also can reduce the complexity of calculating the current source image distance, and decrease calculation quantity.

In other examples, the position relation of the LED array 12 relative to the detector can also be changed, so as to enable the line connecting the geometric center of the LED array 12 and the detection center 181 of the detector to be at other angles relative to the longitudinal line on the detector, so after the center 101 of the tube is aligned with the detection center 181 of the detector 18 in the z-axis direction, in the image displayed by the display 16, the geometric center of the LED array 12 will be located on the line disposed at other degrees relative to the longitudinal line in the image. In this case, the current source image distance can be calculated only transforming the above formula (1) according to new oblique angles.

After the center 101 of the tube is aligned with the detection center 181 of the detector 18, the current source image distance can be accurately calculated through the SID calculation module; the calculated current source image distance, as an important exposure parameter, helps the radiographer to obtain a detection image with higher quality.

Figure 4:
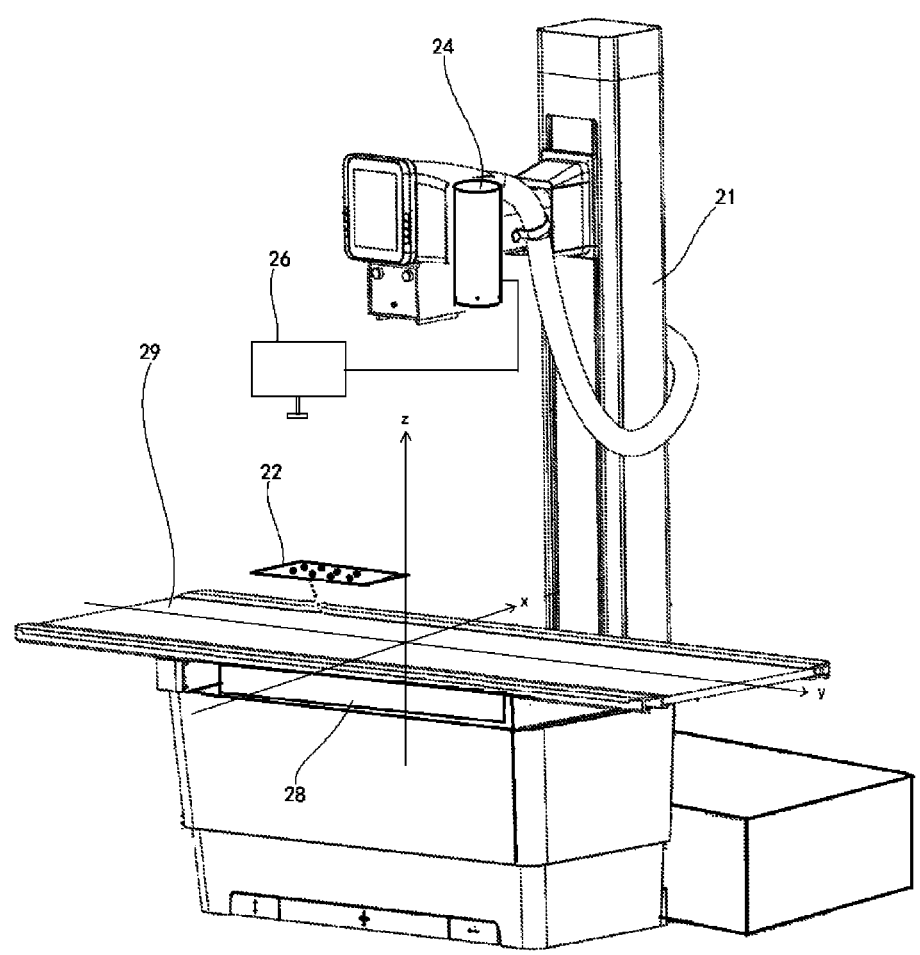
FIG. 4 is a structural diagram of the X-ray equipment provided by another illustrative example of the present invention.
Figure 5:
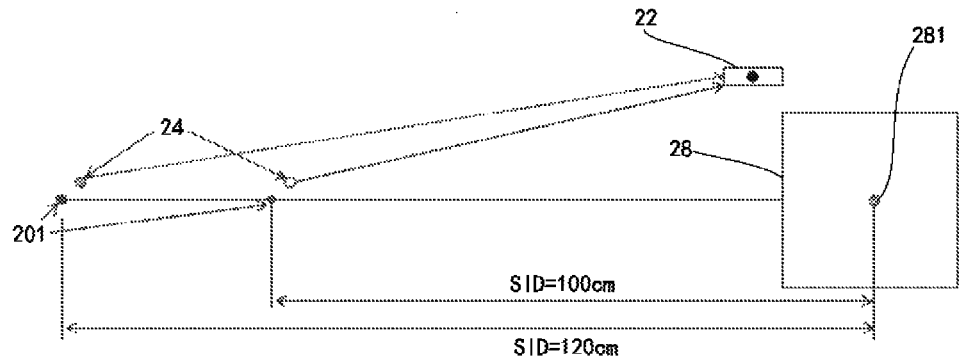
FIG. 5 is an illustrative schematic diagram of the position relation among the camera, the tube, the LED array and the detector in FIG. 4, in the case of different SID values.
Figure 6:
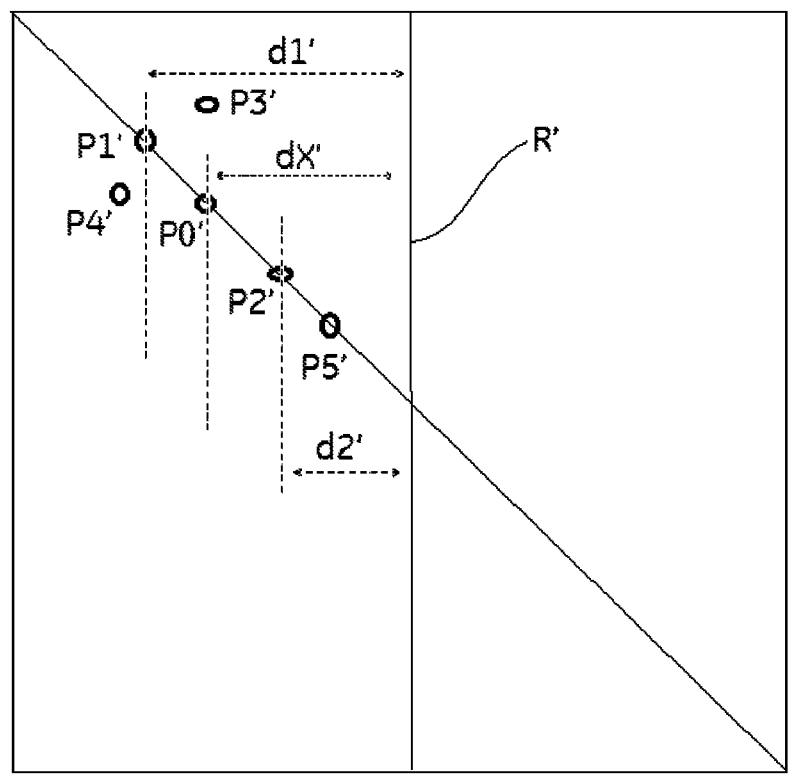
FIG. 6 is an illustrative schematic diagram of relative changes in the position of the geometric center of the LED array on the display, when the relative positions of the center of the tube and the detection center of the detector in FIG. 4 vary.

FIG. 4 is a structural diagram of the X-ray equipment provided by another illustrative example of the present invention; FIG. 5 is an illustrative schematic diagram of the position relation among the camera, the tube, the LED array and the detector in FIG. 4, in the case of different source image distances; FIG. 6 is an illustrative schematic diagram of relative changes in the position of the geometric center of the LED array on the display, when the relative positions of the center of the tube and the detection center of the detector in FIG. 4 vary. As shown in FIGS. 4 to 6, the X-ray equipment in the present example is a horizontal X-ray equipment comprising a tube (not marked) and a detector 28; the tube is mounted on a tube column 21; the detector 28 is mounted on the back of a detection bed 29; the tube has a center 201, and the detector 28 has a detection center 281, which specifically is located on the detection plane of the detector 28. During detection, the center 201 of the tube is aligned with the detection center 281 of the detector 28; after penetrating a detected subject and the detection bed 29, the X-rays that are emitted downwards by the tube along the vertical direction (the z-axis direction in FIG. 4) are detected by the detector 28; image information of a detected site can be formed by treating the detected signals.

The X-ray equipment further comprises an LED array 22, a camera 24 and a display 26. The LED array 22 is fixed relative to the detection center 281 of the detector 28. The camera 24 is fixed relative to the center 201 of the tube, for photographing the LED array 22. The display 26 is connected to the camera 24, for displaying images photographed by the camera 24. Specifically, the display 26 can be connected to the camera 24 via a signal transmission module, and receive images photographed by the camera 24.

Similar to the principles of the vertical X-ray equipment as shown in FIG. 1, since the camera 24 is fixed relative to the center 201 of the tube, and the LED array 22 is fixed relative to the detection center 281 of the detector 28, via a coordinate conversion, the position relation when the center 201 of the tube is aligned relative to the detection center 281 of the detector 28, can be represented by the position of the geometric center of the LED array 22 in the display 26, for convenient depiction, the pixel unit of which position also referring to a "specific pixel unit".

In other words, after the display 26 displays the image photographed by the camera 24, when the center 201 of the tube is aligned relative to the detection center 281 of the detector 28, the geometric center of the LED array 22 is located on the specific pixel unit on the display 26.

As shown in FIG. 6, the position of the specific pixel unit on the display 26 is specifically as follows: located between pixel units P1' and P2' on a line connecting the pixel units P1' and P2'. The pixel unit P1' is: the position of the geometric center of the LED array 22 on the display 26, when the center 201 of the tube is aligned with the detection center 281 of the detector 28, and the source image distance is a lower critical value (e.g., 100 cm); the pixel unit P2' is: the position of the geometric center of the LED array 22 on the display 26, when the center 201 of the tube is aligned with the detection center 281 of the detector 28, and the source image distance is a larger critical value (e.g., 120 cm).

Since the centers of the tube and detector of the horizontal X-ray equipment are generally in a fixed alignment state in the anterior-posterior direction (the x-axis direction as shown by FIG. 4), the present example only involves alignment operations in the y-axis and z-axis directions; if the geometric center of the LED array 22 is on the line connecting the pixel units P1' and P2', it means that the center 201 of the tube has been aligned with the detection center 281 of the detector 28 in the y-axis direction; if the geometric center of the LED array 22 is further located between the pixel units P1' and P2', it means the source image distance of the horizontal X-ray equipment falls within the stipulated range.

On the contrary, as shown in FIG. 6, when the tube is moved to the left along the y-axis direction, the geometric center of the LED array 22 will move to the position as shown by P3' in FIG. 6; when the tube is moved downwards along the y-axis direction, the geometric center of the LED array 22 will move to the position as shown by P4' in FIG. 6; when the tube is moved along the z-axis direction such that the source image distance goes beyond the range which is defined by the above lower critical value and larger critical value, the geometric center of the LED array 22 may move to the position as shown by P5' in FIG. 6.

In the present example, in order to make the relative position relation among the LED array 22, the camera 24, the tube and the detector 28 more simple, so as to simplify the complexity of coordinate conversion, the photographing direction of the camera 24 is set to be identical to the irradiating direction of the tube, and the geometric center of the LED array 22 is defined on the light emitting area thereof. In addition, in order to avoid the detection bed and the body of the detected subject from obstructing the LED array 22, and ensure the camera 24 to photograph the geometric center of the LED array 22 during detection, the LED array 22 in the present example specifically can be fixed on the detector 28 through the fixed arm (not marked) extending from the detector 28, so as to enable the LED array 22 to protrude from the detection bed 29, and the mapping line of the line connecting the geometric center thereof and the detection center 281 on the detection plane is disposed at a specific angle relative to the longitudinal line (i.e., the line on the detector 28 parallel to the y-axis direction in FIG. 4 and the reference line R' in FIG. 6) on the detection plane. Hence, when the center 201 of the tube is aligned with the detection center 281, viewed from the photographing direction of the camera 24, the line connecting the geometric center of the LED array 22 and the detection center 281 is disposed at a specific angle relative to the longitudinal line on the detector.

Alternatively, the X-ray equipment in the present example, further comprises a SID calculation module (not shown) connected to the display 26, for calculating a current source image distance SIDX', based on horizontal pixel offset (dX' as shown in FIG. 6) of the pixel unit (P0' as shown in FIG. 6) on which the geometric center of the LED array 22 is currently located relative to a reference pixel unit (e.g., a pixel unit located on the reference line R' as shown in FIG. 6) preset on the display 26, horizontal pixel offset (d1' as shown in FIG. 6) of the pixel unit P1' relative to the reference pixel unit, and relation between the lower critical value of the source image distance and the larger critical value of the source image distance, under the specific angle.

In the present example, the line connecting the geometric center of the LED array 22 and the detection center 281 of the detector 28 is specifically at an angle of 45 degrees relative to the longitudinal line on the detector 28, so after the center 201 of the tube is aligned with the detection center 281 of the detector 28 in the y-axis direction, in the image displayed by the display 26, the geometric center of the LED array 22 is always located on the line disposed at the angle of 45 degrees relative to the reference line R'. Hence, the SID calculation module specifically can calculate the current source image distance SIDX' according to the following formula (2):

$$SIDX'=SID1'+(SID2'-SID1')/(dX'-d1') \qquad (2).$$

In the above formula, SID X' is the current source image distance of the horizontal X-ray equipment, SID1' is the lower critical value of the source image distance, SID2' is the larger critical value of the source image distance, dX' is the horizontal pixel offset of the pixel unit P0' on which the geometric center of the LED array 22 is currently located relative to the reference pixel unit, and d1' is the horizontal pixel offset of the pixel unit P1' relative to the reference pixel unit.

The setting of the line connecting the geometric center of the LED array 22 and the detection center 281 of the detector 28 to be at an angle of 45 degrees relative to the longitudinal line on the detector 28, not only can avoid the LED array 22 from being obstructed by the detection bed and the detected subject thereon to the maximum extent, and ensure the camera 24 to photograph it, but also can reduce the complexity of calculating the current source image distance, and decrease calculation quantity.

In other examples, the position relation of the LED array 22 relative to the detector can also be changed, so as to adjust the angle of 45 degrees of the line connecting the geometric center of the LED array 22 and the detection center 281 of the detector 28 relative to the longitudinal line on the detector 28 to be other angles, so after the center 201 of the tube is aligned with the detection center 281 of the detector 28 in the y-axis direction, in the image displayed by the display 26, the geometric center of the LED array 22 will be located on the line disposed at other degrees relative to the reference line R'. In this case, the current source image distance can be calculated only transforming the above formula (2) according to new angles.

Figure 7:
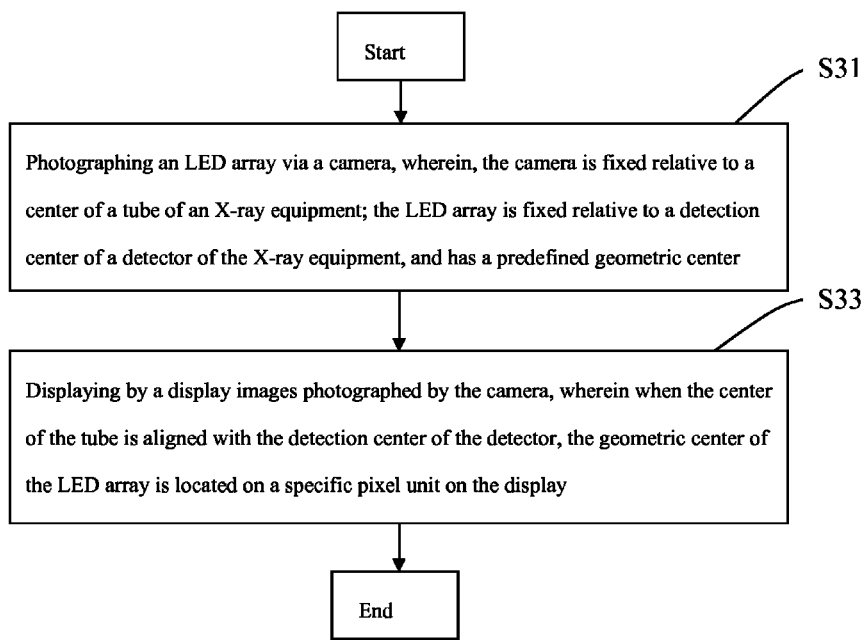
FIG. 7 is a flow diagram of the alignment method of X-ray equipment provided by one illustrative example of the present invention.

FIG. 7 is a flow diagram of the alignment method of X-ray equipment provided by one illustrative example of the present invention. As shown in FIG. 7, the method comprises photographing step S31 and displaying step S33, and can further comprise SID calculating step. The method specifically can be applied into the X-ray equipment as shown in FIG. 1 or FIG. 4, so as to realize precise alignment of the tube and the detector of the X-ray equipment.

The photographing step S31 photographs the LED array via the camera, wherein, the camera is fixed relative to the center of the tube of the X-ray equipment; the LED array is fixed relative to the detection center of the detector of the X-ray equipment, and has a predefined geometric center;

The displaying step S33 displays on the display images photographed by the camera; when the center of the tube is aligned with the detection center of the detector, the geometric center of the LED array is located on the specific pixel unit on the display.

The position of the specific pixel unit is specifically as follows: located between the first pixel unit and the second pixel unit (e.g., pixel units P1 and P2, or, pixel units P1' and P2') on the line connecting the first pixel unit and the second pixel unit;

The first pixel unit and the second pixel unit are respectively as follows: the position of the geometric center of the LED array on the display, when the center of the tube is aligned with the detection center of the detector, and the source image distances are the lower critical value and the larger critical value (e.g. 100 cm and 180 cm, or, 100 cm and 120 cm), respectively.

Alternatively, the line connecting the geometric center of the LED array and the detection center of the detector is disposed at a specific angle relative to the longitudinal line on the detector; in the photographing step S31, the photographing direction of the camera is identical to the irradiating direction of the tube.

The SID calculating step can be performed following the displaying step S33, which calculating step calculates a current source image distance, based on horizontal pixel offset of the pixel unit (e.g., P0 or P0') on which the geometric center of the LED array is currently located relative to a reference pixel unit (e.g., a pixel unit located on the reference line R or R') preset on the display, horizontal pixel offset of the first pixel unit relative to the reference pixel unit, and relation between the lower critical value and the larger critical value of the source image distance, under the specific angle.

Alternatively, the above specific angle is 45 degrees; when it is applied in the X-ray equipment as shown by FIG. 1, the SID calculating step calculates the current source image distance according to the formula (1); when it is applied in the X-ray equipment as shown by FIG. 4, the SID calculating step calculates the current source image distance according to the formula (2).

In the X-ray equipment and the alignment method thereof provided by the illustrative examples of the present invention, the camera is set to be fixed relative to the center of the tube, and the LED array is set to be fixed relative to the detection center of the detector; when the center of the tube is aligned with the detection center of the detector, in the image photographed by the camera which image is displayed by the display, the geometric center of the LED array is located on the specific pixel unit on the display. Hence, the radiographer can align the center of the tube with the center of the detector, only by judging whether the centers of the tube and the detector are aligned by observing the position of the geometric center of the LED array on the display, and with manual or automatic operation; alignment precision is high, and operation is intuitive and convenient, so a better alignment effect is obtained.

After alignment, based on the relation of pixel offset between the pixel unit on which the geometric center of the LED array is currently located and the known pixel unit (e.g., the pixel units on which the geometric center of the LED array is located on the display, when the source image distances are the larger critical value and the lower critical value) under the specific angle, the current source image distance can be further precisely calculated; the calculated current source image distance, as an important exposure parameter, is provided to the radiographer for enhancing the quality of images as photographed.

Some illustrative examples have been depicted above. However, it can be understood that various amendments can be made. For example, if the technology as depicted is executed in a different order, and/or, if the assemblies in the system, framework, device or electric circuit as depicted are combined in a different manner and/or substituted or supplemented by additional assemblies or their equivalents, an appropriate result can be achieved. Accordingly, other embodiments all fall within the protection scopes of the claims.

What is claimed is:

1. An X-ray equipment, comprising:
   a tube and a detector;
   an LED array fixed relative to a detection center of the detector, the LED array having a predefined geometric center;
   a camera fixed relative to a center of the tube, for photographing the LED array; and
   a display connected to the camera, for displaying images photographed by the camera, wherein when the center of the tube is aligned with the detection center of the detector, the geometric center of the LED array is located on a specific pixel unit on the display,
   wherein the specific pixel unit is located between a first pixel unit and a second pixel unit on a line connecting the first pixel unit and the second pixel unit, and the first pixel unit and the second pixel unit are positions of the geometric center of the LED array on the display when the center of the tube is aligned with the detection center of the detector and source image distances are a lower critical value and a larger critical value, respectively.

2. The X-ray equipment according to claim 1, wherein the photographing direction of the camera is identical to the irradiating direction of the tube, and when the center of the tube is aligned with the detection center of the detector, viewed from the photographing direction of the camera, the line connecting the geometric center of the LED array and the detection center of the detector is disposed at a specific angle relative to a longitudinal line on the detector.

3. The X-ray equipment according to claim 2, wherein the light emitting area of the LED array is located in a same plane with the detection center of the detector.

4. The X-ray equipment according to claim 1, wherein the geometric center of the LED array is defined on a light emitting area thereof.

5. The X-ray equipment according to claim 1, wherein the LED array is fixed on the detector through a fixed arm extending from the detector.

6. The X-ray equipment according to claim 1, wherein the camera is mounted on a beam limiter fixedly arranged relative to the tube.

7. The X-ray equipment according to claim 1, wherein the photographing direction of the camera is identical to the irradiating direction of the tube, and when the center of the tube is aligned with the detection center of the detector, viewed from the photographing direction of the camera, the line connecting the geometric center of the LED array and the detection center of the detector is disposed at a specific angle relative to a longitudinal line on the detector.

8. The X-ray equipment according to claim 7, further comprising a SID calculation module connected to the display and configured to calculate a current source image distance based on horizontal pixel offset of a pixel unit on which the geometric center of the LED array is currently located relative to a reference pixel unit preset on the display, a horizontal pixel offset of the first pixel unit relative to the reference pixel unit, and a relation between the lower critical value and the larger critical value of the source image distance, under the specific angle.

9. The X-ray equipment according to claim 1, wherein the geometric center of the LED array is defined on a light emitting area thereof.

10. The X-ray equipment according to claim 1, wherein the LED array is fixed on the detector through a fixed arm extending from the detector.

11. The X-ray equipment according to claim 1, wherein the camera is mounted on a beam limiter fixedly arranged relative to the tube.

12. An X-ray equipment, comprising:
a tube and a detector;
an LED array fixed relative to a detection center of the detector, the LED array having a predefined geometric center;
a camera fixed relative to a center of the tube, for photographing the LED array;
a display connected to the camera, for displaying images photographed by the camera, wherein when the center of the tube is aligned with the detection center of the detector, the geometric center of the LED array is located on a specific pixel unit on the display; and
a SID calculation module connected to the display and configured to calculate a current source image distance based on horizontal pixel offset of a pixel unit on which the geometric center of the LED array is currently located relative to a reference pixel unit preset on the display, a horizontal pixel offset of the first pixel unit relative to the reference pixel unit, and a relation between the lower critical value and the larger critical value of the source image distance, under a specific angle relative to a longitudinal line on the detector,
wherein the photographing direction of the camera is identical to the irradiating direction of the tube, and when the center of the tube is aligned with the detection center of the detector, viewed from the photographing direction of the camera, the line connecting the geometric center of the LED array and the detection center of the detector is disposed at the specific angle.

13. The X-ray equipment according to claim 12, wherein the specific angle is 45 degrees, and the calculation module calculates the current source image distance of the X-ray equipment according to the following formula:

$$SIDX = SID1 + (SID2 - SID1)/(dX - d1)$$

wherein SIDX is the current source image distance, SID1 is the lower critical value of the source image distance, SID2 is the larger critical value of the source image distance, dX is the horizontal pixel offset of the pixel unit on which the geometric center of the LED array is currently located relative to the reference pixel unit, and d1 is the horizontal pixel offset of the first pixel unit relative to the reference pixel unit.

14. An alignment method of X-ray equipment comprising:
photographing an LED array via a camera wherein the camera is fixed relative to a center of a tube of an X-ray equipment, and the LED array is fixed relative to a detection center of a detector of the X-ray equipment and has a predefined geometric center; and
displaying via a display images photographed by the camera, wherein when the center of the tube is aligned with the detection center of the detector, the geometric center of the LED array is located on a specific pixel unit on the display,
wherein the specific pixel unit is located between a first pixel unit and a second pixel unit on a line connecting the first pixel unit and the second pixel unit, and the first pixel unit and the second pixel unit are positions of the geometric center of the LED array on the display when the center of the tube is aligned with the detection center of the detector and source image distances are a lower critical value and a larger critical value, respectively.

15. The alignment method of X-ray equipment according to claim 14, wherein in the photographing step, the photographing direction of the camera is identical to the irradiating direction of the tube, and when the center of the tube is aligned with the detection center of the detector, viewed from the photographing direction of the camera, the line connecting the geometric center of the LED array and the detection center of the detector is disposed at a specific angle relative to a longitudinal line on the detector.

16. An alignment method of X-ray equipment comprising:
photographing an LED array via a camera wherein the camera is fixed relative to a center of a tube of an X-ray equipment, and the LED array is fixed relative to a detection center of a detector of the X-ray equipment and has a predefined geometric center; and
displaying via a display images photographed by the camera, wherein when the center of the tube is aligned with the detection center of the detector, the geometric center of the LED array is located on a specific pixel unit on the display,
wherein in the photographing step, the photographing direction of the camera is identical to an irradiating direction of the tube, and when the center of the tube is aligned with the detection center of the detector, viewed from the photographing direction of the camera, the line connecting the geometric center of the LED array and the detection center of the detector is disposed at a specific angle relative to a longitudinal line on the detector.

17. The alignment method of X-ray equipment according to claim 16, further comprising:
calculating a current source image distance based on horizontal pixel offset of a pixel unit on which the geometric center of the LED array is currently located relative to a reference pixel unit preset on the display, a horizontal pixel offset of the first pixel unit relative to the reference pixel unit, and a relation between the lower critical value and the larger critical value of the source image distance, under the specific angle.

18. The alignment method of X-ray equipment according to claim 17, wherein the specific angle is 45 degrees, and the SID calculating step calculates the current source image distance according to the following formula:

$$SIDX = SID1 + (SID2 - SID1)/(dX - d1)$$

wherein, SIDX is the current source image distance, SID1 is the lower critical value of the source image distance, SID2 is the larger critical value of the source image distance, dX is the horizontal pixel offset of the pixel unit on which the geometric center of the LED array is currently located relative to the reference pixel unit, and d1 is the horizontal pixel offset of the first pixel unit relative to the reference pixel unit.

* * * * *